US012008163B1

(12) United States Patent
Manchem et al.

(10) Patent No.: US 12,008,163 B1
(45) Date of Patent: Jun. 11, 2024

(54) EARBUD SENSOR ASSEMBLY

(71) Applicant: NAQI LOGIX INC., Vancouver (CA)

(72) Inventors: R K K Durga Rao Manchem, Hyderbad (IN); Sanandan Sudhir, Ahmedabad (IN); Jaymin Oza, Ahmedabad (IN); Prayas Rokde, Ahmedabad (IN); David Segal, York, PA (US)

(73) Assignee: NAQI LOGIX INC., Vancouver (CA)

( * ) Notice: Subject to any disclaimer, the term of this patent is extended or adjusted under 35 U.S.C. 154(b) by 0 days.

(21) Appl. No.: 18/178,968

(22) Filed: Mar. 6, 2023

(51) Int. Cl.
*G06F 3/01* (2006.01)
*A61B 5/00* (2006.01)
*A61B 5/256* (2021.01)

(52) U.S. Cl.
CPC .............. *G06F 3/015* (2013.01); *A61B 5/256* (2021.01); *A61B 5/6817* (2013.01); *G06F 3/017* (2013.01); *A61B 2562/0209* (2013.01); *A61B 2562/04* (2013.01)

(58) Field of Classification Search
CPC ......... G06F 3/015; A61B 5/291; A61B 5/398; A61B 5/296; A61B 5/369; A61B 5/389
See application file for complete search history.

(56) References Cited

U.S. PATENT DOCUMENTS

| | | |
|---|---|---|
| 9,405,366 B2 | 8/2016 | Segal |
| 10,126,816 B2 | 11/2018 | Segal |
| 10,275,027 B2 | 4/2019 | Segal |
| 10,852,829 B2 * | 12/2020 | Rüdiger .............. H04R 1/1016 |
| 11,494,001 B2 | 11/2022 | Sirois et al. |
| 2006/0094974 A1 * | 5/2006 | Cain ..................... A61B 5/291 600/545 |
| 2010/0239114 A1 * | 9/2010 | Wada ................... A61B 5/6817 381/380 |
| 2019/0192077 A1 * | 6/2019 | Kaiser .................... G06F 3/015 |
| 2019/0282119 A1 * | 9/2019 | Andersen .............. A61B 5/256 |
| 2020/0184735 A1 * | 6/2020 | Pridie ................. G06F 3/0346 |
| 2022/0031217 A1 * | 2/2022 | Kidmose .............. A61B 5/6817 |
| 2022/0276723 A1 * | 9/2022 | Sirois .................. H04R 1/1041 |
| 2022/0394396 A1 * | 12/2022 | Gallégo ................ A61B 5/296 |
| 2023/0225659 A1 * | 7/2023 | Azemi .................... A61B 5/31 600/383 |

FOREIGN PATENT DOCUMENTS

WO 2021234603 A1 11/2021

OTHER PUBLICATIONS

International Search Report and Written Opinion of The International Searching Authority issued in International Appl. No. PCT/IB/2023/052092, 9 pages, dated Nov. 17, 2023.

Lee et al. (2018), "Anthropometric analysis of 3D ear scans of Koreans and Caucasians for ear product design," Ergonomics, 61(11), 1480-1495, (2018).

\* cited by examiner

*Primary Examiner* — Koosha Sharifi-Tafreshi
(74) *Attorney, Agent, or Firm* — DLA Piper LLP US

(57) ABSTRACT

Systems and methods for controlling devices through gestures sensed via an earbud. The earbud can include a set of electrodes configured to contact particular anatomic locations on an individual's ear. Based on electrophysiologic signals sensed via the electrode assembly, the system can identify gestures being performed by the user and control the external device accordingly.

13 Claims, 11 Drawing Sheets

EARBUD SENSOR ASSEMBLY

BACKGROUND

As electronic devices become increasingly ubiquitous, it has become necessary to identify alternative ways for controlling those devices that do not rely on traditional input methods because such traditional methods can be cumbersome and inefficient during everyday use. So-called "human interface" technologies have turned towards using the individual himself or herself as the input means, eschewing the need for additional, dedicated input devices to control another electronic device. Therefore, being able to control electronic devices via gestures and other intuitive, subtle control schemes could be highly beneficial and convenient. Earbuds present a unique opportunity for implementing such gesture-based control schemes. An earbud is much more discreet and portable than a head-mounted sensor and can be worn throughout the day without causing discomfort. Additionally, an earbud's proximity to the ear canal provides better signal quality and accuracy for many applications compared to a head-mounted sensor, which can be affected by movement and other external factors. Accordingly, control schemes implemented via an earbud having the capability to sense electrophysiologic signals or other biosignals could allow for the control of music playback, phone calls, and voice assistants in a handsfree manner, which would provide a versatile and convenient device for monitoring health and wellness. In addition to convenience, effective human interface technologies can allow injured or disabled individuals to more effectively control their electronic devices, thereby improving their ability interact with other devices without additional assistance from others or the use of assistive technologies.

SUMMARY

The present disclosure is directed to devices, such as earbuds, that are wearable by users and adapted for detecting gestures and/or actions being performed by the users. In particular, the present disclosure is directed to sensor assemblies for such devices.

In one embodiment, there is provided an earbud comprising: a first electrode positioned to physically contact a first anatomic location of an ear of a user when the earbud is worn by the user; a second electrode positioned to physically contact a second anatomic location of the ear when the earbud is worn by the user; a third electrode positioned to physically contact a third anatomic location of the ear when the earbud is worn by the user; and a controller coupled to the first electrode, the second electrode, and the third electrode, the controller programmed to: receive an electrophysiologic measurement from each of the first electrode, the second electrode, and the third electrode, determine a gesture being performed by the user based on the received electrophysiologic measurements, and transmit the determined gesture to an external device for control thereof.

In one embodiment, there is provided a system comprising: an earbud comprising: a first electrode positioned to physically contact a first anatomic location of an ear of a user when the earbud is worn by the user, a second electrode positioned to physically contact a second anatomic location of the ear when the earbud is worn by the user, a third electrode positioned to physically contact a third anatomic location of the ear when the earbud is worn by the user, and a controller coupled to the first electrode, the second electrode, and the third electrode, the controller programmed to: receive an electrophysiologic measurement from each of the first electrode, the second electrode, and the third electrode, and determine a gesture being performed by the user based on the received electrophysiologic measurements; an external device communicably coupled to the earbud, the external device programmed to: receive the determined gesture from the controller of the earbud, and perform an action in response to the determined gesture.

In one embodiment, there is provided an earbud comprising: a first electrode positioned to physically contact a first anatomic location of an ear of a user when the earbud is worn by the user, the first anatomic location exhibiting a high degree of electrophysiologic activity; a second electrode positioned to physically contact a second anatomic location of the ear when the earbud is worn by the user, the second anatomic location exhibiting a low degree of electrophysiologic activity; a third electrode positioned to physically contact a third anatomic location of the ear when the earbud is worn by the user, the third anatomic location exhibiting a low degree of electrophysiologic activity and being physically separated from the first electrode and the second electrode; and a controller coupled to the first electrode, the second electrode, and the third electrode, the controller programmed to: receive an electrophysiologic measurement from each of the first electrode, the second electrode, and the third electrode, determine a gesture being performed by the user based on the received electrophysiologic measurements, transmit the determined gesture to an external device for control thereof.

In some embodiments of the earbud and/or system, wherein the electrophysiologic measurements are selected from the group consisting of electrocardiogram (ECG), an electroencephalogram (EEG), or an electromyography (EMG).

In some embodiments of the earbud and/or system, each of the first electrode, the second electrode, and the third electrode comprise a size from about 5 mm to about 6 mm.

In some embodiments of the earbud and/or system, the external device comprises a virtual reality headset.

In some embodiments of the earbud and/or system, each of the first electrode, the second electrode, and the third electrode comprise at least one of an elastomer, silicone, a metal, a ceramic, a carbon nanotube material, composites thereof, or combinations thereof.

In some embodiments of the earbud and/or system, the first anatomic location comprises a concha, the second anatomic location comprises a tragus, and the third anatomic location comprises a triangular fossa.

In some embodiments of the earbud and/or system, the first anatomic location comprises a concha, the second anatomic location comprises a triangular fossa, and the third anatomic location comprises a helix.

In some embodiments of the earbud and/or system, the first anatomic location, the second anatomic location, and the third anatomic location are selected such that they correspond to at least two different nerves.

FIGURES

DETAILED DESCRIPTION

Described herein are devices for detecting, receiving, processing, and recording various biological signals, such as electrophysiologic signals, that can in turn be used to control other objects/devices and communicate with other objects and/or other humans. In some embodiments, the devices described herein can be embodied as earbuds.

Systems for User Gestural Identification

Figure 1A:
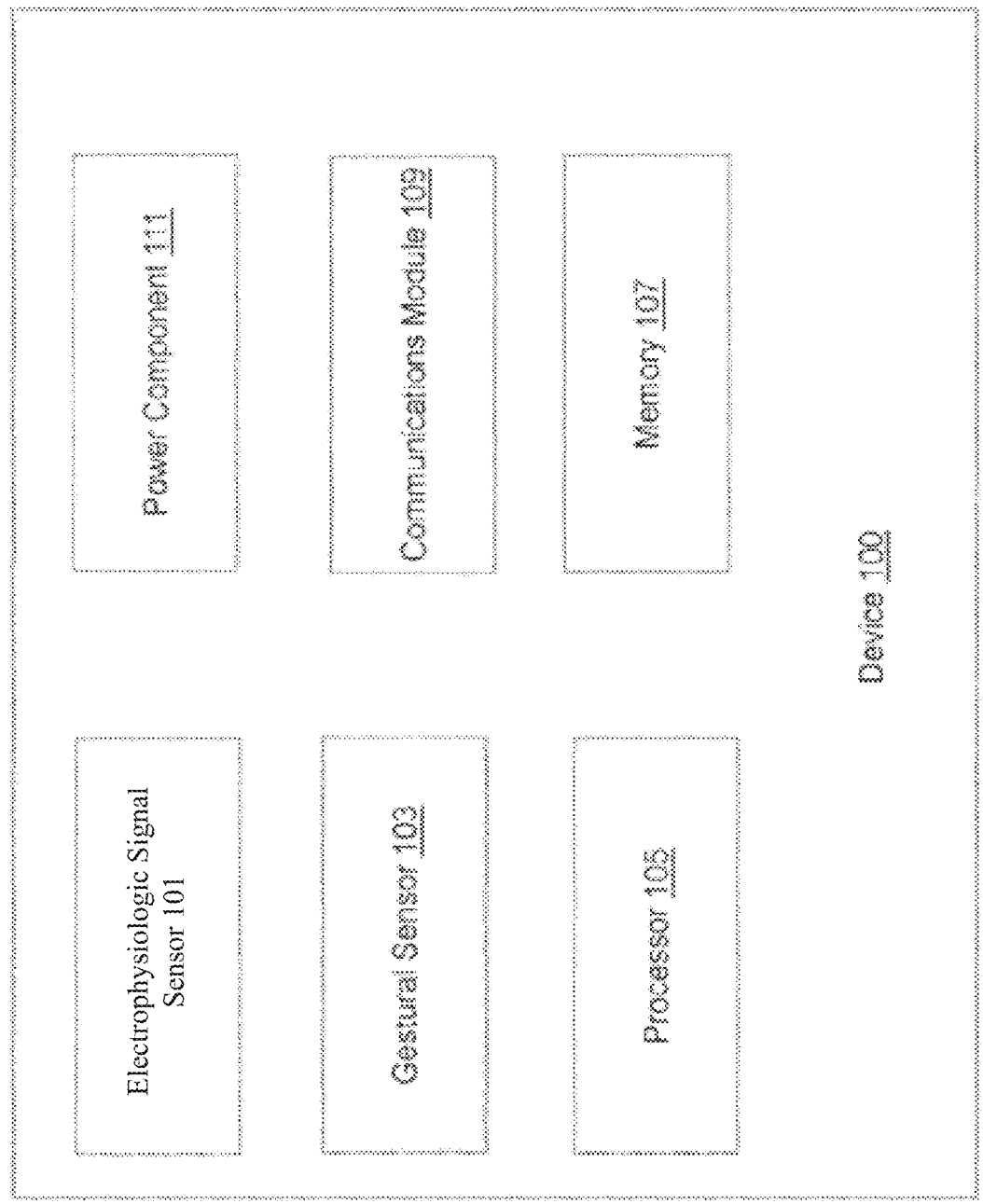
FIG. 1A depicts a block diagram of a device for user gestural identification, in accordance with an embodiment of the present disclosure.

FIG. 1A illustrates the components of an exemplary device 100. The device 100 may include an electrophysiologic signal sensor 101 configured to detect, receive, process, convert, record, and/or transmit electrophysiological data. In some embodiments, the electrophysiologic signal sensor 101 could include an EMG sensor, an ECG sensor, or an EOD sensor. In some embodiments, the device 100 could further include various combinations of electrophysiologic signal sensors 101. The device 100 may also include a gestural sensor 103 configured to detect, receive, process, convert, record, and/or transmit data that is indicative of gestures being performed by the wearer. In some embodiments, the gestural sensor 103 could include a gyroscope, an accelerometer, or a pressure sensor configured to detect an inner ear pressure of the wearer. In some embodiments, the device 100 could further include various combinations of gestural sensors 103. The device 100 may also include a processor 105 configured to detect, receive, process, convert, record, and/or transmit electrophysiological data obtained via the electrophysiologic signal sensor 101 and the gestural data obtained via the gestural sensor 103. The processor 105 may be controlled by software located on non-transitory memory 107 stored on the device 100. The device 100 may also include a communications module 109 configured to detect, receive, process, convert, record, and/or transmit data from the device 100 to anyone of a plurality of separate devices and/or humans. The components of the device 100 may be powered by one or more power components 111.

In one illustrative embodiment, the electrophysiologic signal sensor 101, the gestural sensor 103, the processor 105, non-transitory memory 107, and communications module 109 may be contained within the device 100. In one illustrative embodiment, the device 100 may take the shape of an earbud or similar device. In such an embodiment, at least a portion of the device 100 may be configured to fit within the ear canal of a user. In another illustrative embodiment, the device 100 may be worn covertly. For example, the device 100 may not be visible to someone interacting with the user (i.e., covert).

In some embodiments, the electrophysiologic signal sensor 101 can be configured to detect a variety of electrophysiologic signals or biological electrical activity, such as a mu rhythm, an EMG, an ECG, an EOD, an electroencephalogram (EEG), a magnetic electroencephalograms (MEG), and the like. The electrophysiologic signal sensor 101 may be configured to obtain any type of electrophysiological data from a user. The electrophysiologic signal sensor 101 may include one or more electrodes configured to project into the ear canal and in the operative vicinity of the user to record electrophysiological data from being in contact with the user. In some embodiments, the device 100 is configured to detect, receive, process, convert, record, and/or transmit gestural data to control other objects, devices and/or with other objects/devices and/or other humans. In one embodiment, the electrophysiologic signal sensor 101 may record electrophysiological activity from the temple, behind the user's ear, and/or the mastoid region.

In one embodiment, the electrophysiologic signal sensor 101 may include at least one active dry electrode. For example, an electrophysiologic signal sensor 101 may be configured to record from on the temple or behind the ear on the mastoid. The placement of the electrophysiologic signal sensor 101 may be optimized to detect, for example, but not limited to, a jaw clench or the like.

In some embodiments, the gestural sensor 103 may include one or more of an accelerometer, gyroscope, and the like. The gestural sensor 103 may provide head tracking by recording rotational, altitude, acceleration vectors, movements, and the like. The gestural sensor 103 may record movements from a location, such as, for example, but not limited to, the operative vicinity of a user. In one embodiment, each of the accelerometer and gyroscope may record movements along three axes. In an embodiment where the gestural sensor 103 includes both an accelerometer and a gyroscope, the gestural sensor 103 may record movement along six axes (i.e., three from each of the gyroscope and accelerometer). In one illustrative embodiment, the gyroscope is a micro-gyroscope. In another embodiment, movements recorded by the gyroscope and/or accelerometer may include head turns, head tilts, head nods, and the like. Accordingly, data detected by these embodiments of the gestural sensor 103 can be used to identify a variety of different gestures being performed by the user.

In some embodiments, the gestural sensor 103 may include an inner ear pressure sensor that is configured to detect changes in the inner ear pressure of a user. The inner ear pressure of a user may change in accordance with the balance and movement of the user. Accordingly, the inner ear pressure sensor may provide additional information regarding gestural behavior. Head turns, head tilts, head nods, jaw clenches, and behaviors can cause changes in inner ear pressure that are detectable by the inner ear pressure sensor. Accordingly, data detected by these embodiments of the gestural sensor 103 can be used to identify a variety of different gestures being performed by the user.

In some embodiments, the device 100 can include various combinations of gestural sensors 103. For example, the device 100 could include both a gyroscope and an inner ear pressure sensor. Accordingly, data from the combination of gestural sensors 103 could be used in conjunction with each other to identify gestures being performed by the user or to individually identify different gestures.

By using gestural data obtained by the gestural sensor 103, the device 100 is able to address the challenges presented by conventional devices that aim to detect, receive, process, convert, record, and transmit electrophysiological and gestural data for control of other objects/devices and communication with other objects/devices and/or other humans. Information from gestural sensors 103 (e.g., accelerometers and micro-gyroscopes) may include recorded movement. Recorded movement allows for a more accurate and faster input and is universal between users.

Additionally, while the speed in detecting and interpreting EEG data may sometimes be slow, gestural data such as those obtained from gestural sensors, such as accelerometers, micro-gyroscopes and/or inner ear pressure monitors, is available almost immediately and is often easier to interpret accurately than EEG data. Furthermore, while conventional systems that convert brain waves such as imagined directions into signals used for control of other objects/devices and communication with other objects/devices and/or other humans are often dependent on a user's ability to imagine directions, and often brain waves associated with one direction are often more pronounced and strongly differentiable than brain waves associated with a different direction.

By contrast, gestural data that can be acquired by gestural sensors (e.g., micro-gyroscopes, accelerometers, and/or inner ear pressure sensors) are able to detect motions performed by users equally in all directions. Accordingly, the device 100 has many benefits over current conventional systems by using both gestural data and EEG data to detect, receive, process, convert, record, and/or transmit electrophysiological gestural data to control other objects/devices and with other objects/devices and/or other humans.

The processor 105 may control the operation of the electrophysiologic signal sensor 101, gestural sensor 103, communications module 109, and any other additional components of the device 100. The processor 105 may be controlled by software instructions (and the like) stored on non-transitory memory 107 of the device 100.

The components of the device 100 including the electrophysiologic signal sensor 101, gestural sensor 103, processor 105, communication module 109, non-transitory memory 107, and the like may be powered by way of the power component 111. In one embodiment, the power component 111 may include batteries and/or rechargeable batteries and the like.

In some embodiments, the communication module 109 may include components to transmit data and information from the device 100 to a separate device. Data and information may be transmitted in any suitable format including wireless and wired communication. The data and information may be transmitted in accordance with any suitable security protocol and the like. The communication module 109 may also receive data and information from separate devices that include signals to control the operation of the device 100. In one embodiment, the communication module 109 may first receive software updates that are later used to update software code stored on the non-transitory memory 107 of the device. In one embodiment, the communication module 109 may receive signals from a separate device that control the operation of the device 100, including signals that cause one or more components of the device 100 to vibrate, illuminate, emit sound, or the like. The vibrations, illuminations, sounds, may be used by the separate device to communicate with other objects/devices and/or other humans with a user of the device 100.

Electrophysiological data recorded by the electrophysiologic signal sensor 101 may be processed at the electrophysiologic signal sensor 101 and/or at the processor 105 prior to being transmitted by the communication module 109 from device 100 to a separate device. Gestural data recorded by the gestural sensor 103 may be processed at the gestural sensor 103 and/or at the processor 105 prior to being transmitted by the communication module 109 from device 100 to a separate device. Processing may include isolating one or more signals or waveform of interest by applying filters, algorithms, signal processing techniques, and the like. Alternatively, the raw data recorded by each of the gestural sensor 103 and electrophysiologic signal sensor 101 may be transmitted without any processing to the separate device, such as, for example, micro device, mobile device or computer by way of the communication module 109. In this manner, the latencies associated with processing the raw data may be avoided.

The gestural data recorded by the gestural sensor 103 and the electrophysiological signal data recorded by the electrophysiological signal sensor 101 can be utilized to identify gestures and/or motions being performed by the user (i.e., the wearer of the device 100). The data obtained by the electrophysiological signal sensor 101 and gestural sensor 103 can be processed by the processor 105. In some embodiments, the gestures and/or motions can be identified onboard the device 100 via the processor 105. In other embodiments, the gestural and/or electrophysiological data can be transmitted via the communication module 109 to a separate device (e.g., a cloud computing system) that is configured or programmed to identify the gestures and/or motions from the data.

Electrophysiological gestural data can be transmitted by the device 100 to a separate device. In one embodiment, the separate device may include one or more computers with one or more processors and non-transitory memory. The separate device may be a laptop, desktop, tablet, cell phone, or the like. The separate device may receive the electrophysiological and/or gestural data corresponding to gestures performed by the user. The user data may be used to control the operation of a software application for communication located at the separate device. In one embodiment, the separate device either automatically or by way of user input, may transmit a signal to the device 100 responsive to translating the gestural data.

Figure 1B:
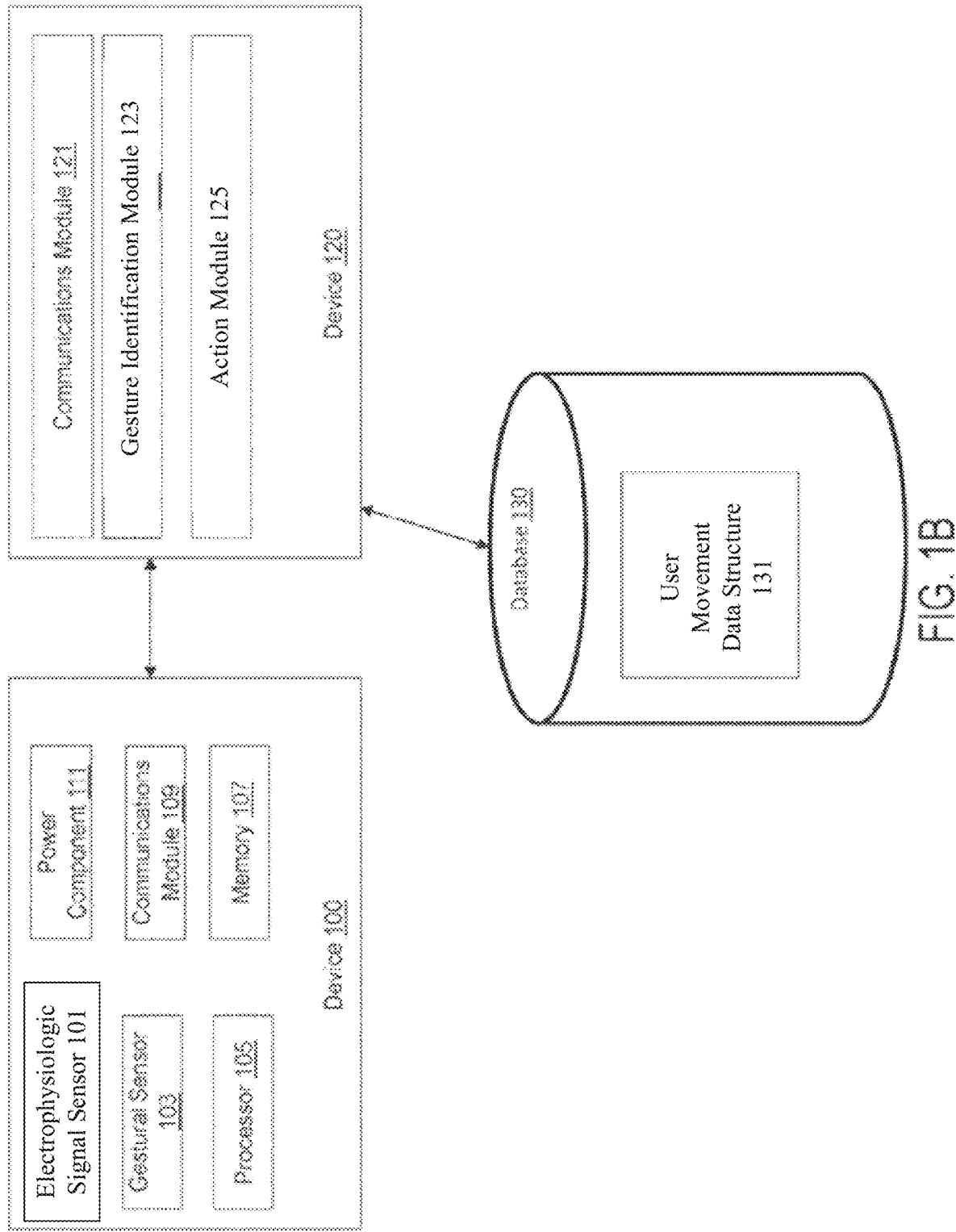
FIG. 1B depicts a block diagram of a system incorporating the device shown in FIG. 1A, in accordance with an embodiment of the present disclosure.

FIG. 1B illustrates an exemplary embodiment of a system using the device of FIG. 1A. As illustrated, the device 100 may be communicatively coupled via communications module 109 to a second device 120. The second device 120 may include a communication module 121 that can receive gestural and/or electrophysiological data sensed by the device 100, a gesture identification module 123, and an action module 125. The second device 120 may be coupled to a database 130. The database 130 may include a user movement data structure 131. The gesture identification module 123 may be configured to aggregate and process gestural and electrophysiological data received from the device 100. The process for aggregating and processing gestural and EEG signals may be in accordance with what is described by U.S. Pat. No. 9,405,366, titled SYSTEMS AND METHODS FOR USING IMAGINED DIRECTIONS TO DEFINE AN ACTION, FUNCTION OR EXECUTION FOR NON-TACTILE DEVICES, filed Jun. 14, 2014, which is hereby incorporated by reference herein in its entirety. Once the gestural and electrophysiological data are transformed and converted into an identified gesture, the action module 125 may access the database 130 to retrieve information regarding the actions corresponding to the gesture from the user movement data structure 131. In one embodiment, the action module 125 can cause the device 120 to perform one or more actions based on the identified user gesture. Example actions may include transmitting a signal to the first device 100 to cause the first device 100 to vibrate, illuminate, emit sound, or the like. In some embodiments, the action module 125 may use the communications module 121 to transmit a signal to the first device 100. In one embodiment, the device 120 may include a user interface that is configured to display, based on control by the action module 125, a message or emit a sound corresponding to the identified gesture based on the information retrieved from the user movement data structure 131. In one embodiment, the action may correspond to sending a signal to control the operation of one or more devices distinct from device 120 and/or device 100.

Figure 2:
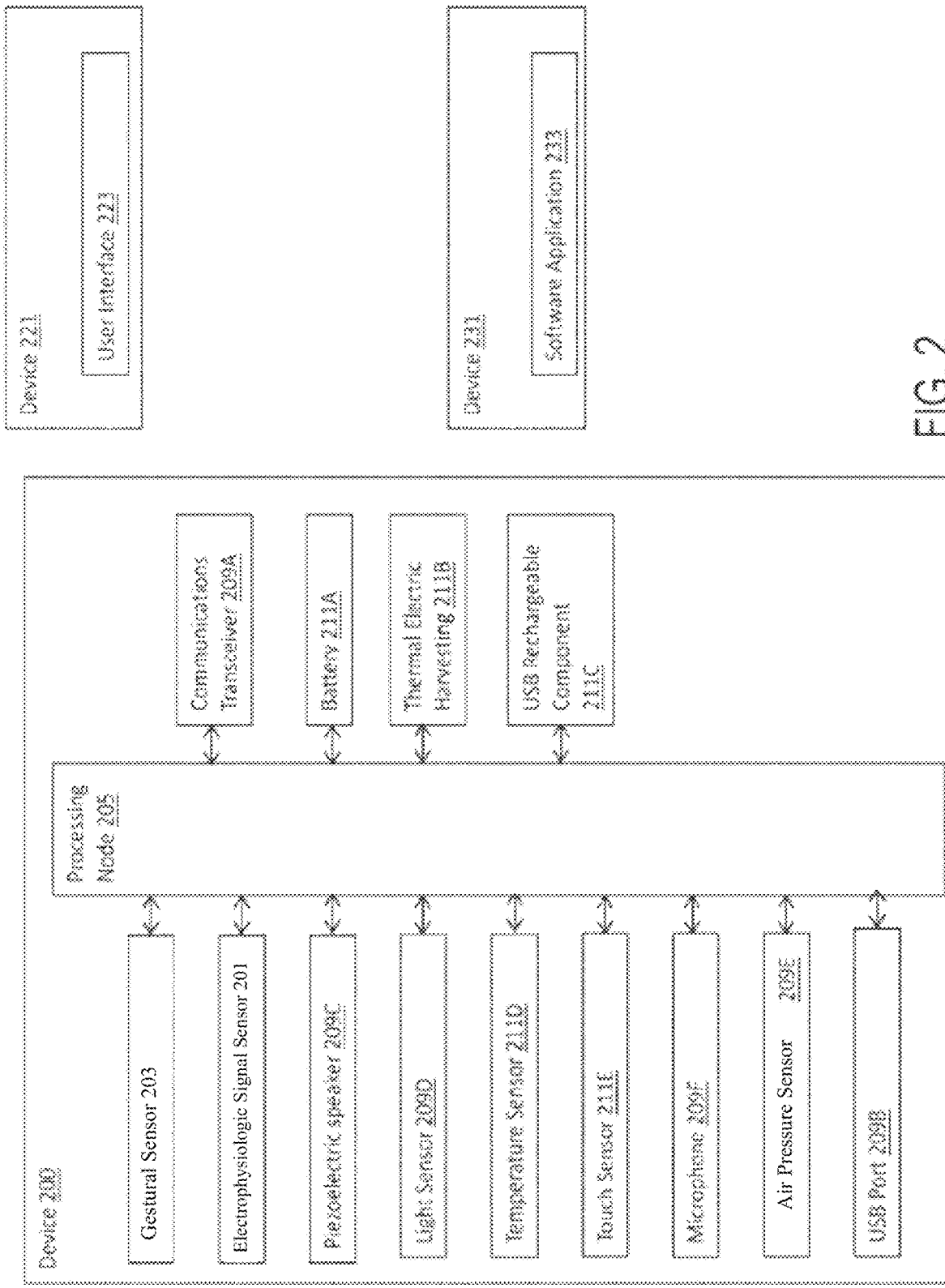
FIG. 2 depicts another block diagram of a device for user gestural identification, in accordance with an embodiment of the present disclosure.

FIG. 2 illustrates another exemplary embodiment of the device 200 which may include one or more of the following elements (without limitation): a gestural sensor 203 (e.g., a micro-gyroscope), an electrophysiologic signal sensor 201, a piezoelectric speaker 209C, a light sensor 209D, a temperature sensor 211D, a touch sensor, 211E, a microphone 209F, an air pressure sensor 209E, a USB port 209B, a communications transceiver 209A, a battery 211A, a thermal electric harvesting component 211B, and a USB rechargeable charger 211C. As illustrated, the components of device 200 may be communicatively coupled by way of a processing node 205. The components of the device 200 may be coupled to a printed circuit board.

In one embodiment, the electrophysiologic signal sensor 201 may be a 100 mV signal sensor with an operational amplifier. In one embodiment, the temperature sensor 211D may be a negative temperature coefficient (NTC) temperature sensor. In one embodiment, the piezoelectric speaker 209C may receive audio signals from a separate device 221, 231 by way of a communications transceiver 209A. In one embodiment the communications transceiver 209A may be a Bluetooth® transceiver. Upon receiving such a signal, the piezoelectric speaker 209C may emit an audio signal to the user of the device 200.

A communications module may include the communications transceiver 209A (e.g., Bluetooth® transceiver). The communications transceiver 209A could be configured to stream data and information from the gestural sensor 203 and/or the electrophysiologic signal sensor 201. The communications transceiver 209A could also be configured to stream digital audio between the user of the device 200 and a separate device 221, 231. The communication module of device 200 may also include a USB port 209B that is configured to link to a separate device via a wireless or wired connection. The USB port 209B may be configured to receive software updates for the components of the device 200.

In one embodiment, the battery 211A may be an alkaline battery that is configured to generate all the voltages required by the sensors 203, 201, components of the communication module including speakers 209C, communications transceiver 209A, USB port 209B, and the like. Optionally, the power component, battery 211A may be rechargeable by way of a near-field charger and/or USB rechargeable component 211C. Alternatively, the battery 211A may also be rechargeable by way of a thermal electric harvesting component 211B. Power to the components of the device 200 from the battery 211A may be managed by a button or the like.

The exemplary embodiment of the device 200 depicted in FIG. 2 may wirelessly transmit gestural signals and EEG signals to separate devices such as a computer system 221 operating in a software environment specially configured with an application interface to control operation of the device 200. The computer system 221 may also include a user interface 223, debugging software, testing software, other health monitoring applications, and the like.

The exemplary embodiment of the device 200 depicted in FIG. 2 may also wirelessly (by way of Bluetooth® or other means) transmit gestural and electrophysiologic signals to a separate portable device 231, such as a cell phone, tablet, or the like. The separate portable device 231 may be operating an application 233 specially configured to control the operation of the device 200.

Additional information regarding earbud sensor assemblies and methods for gesture identification and control can be found in U.S. Pat. No. 10,275,027, titled APPARATUS, METHODS, AND SYSTEMS FOR USING IMAGINED DIRECTION TO DEFINE ACTIONS, FUNCTIONS, OR EXECUTION, issued Apr. 30, 2019 and U.S. Pat. No. 10,126,816, titled SYSTEMS AND METHODS FOR USING IMAGINED DIRECTIONS TO DEFINE AN ACTION, FUNCTION OR EXECUTION FOR NON-TACTILE DEVICES, issued Nov. 13, 2018, each of which is hereby incorporated by reference herein in its entirety.

Earbud Sensor Assemblies for Electrophysiologic Signals

Described herein are various embodiments of earbuds that include sensor assemblies that sense electrophysiologic signals and other biosignals, which can be used to assist in the identification of gestures that the user is performing. Electrophysiologic signals can include, for example, an electrocardiogram (ECG), an electroencephalogram (EEG), or an electromyography (EMG) signal. The sensed gestures can accordingly be used to control a variety of different connected devices, such as virtual reality headsets. The earbud sensor assemblies can be incorporated into the systems and devices described above and shown in connection with FIGS. 1A-2.

Figure 3A:
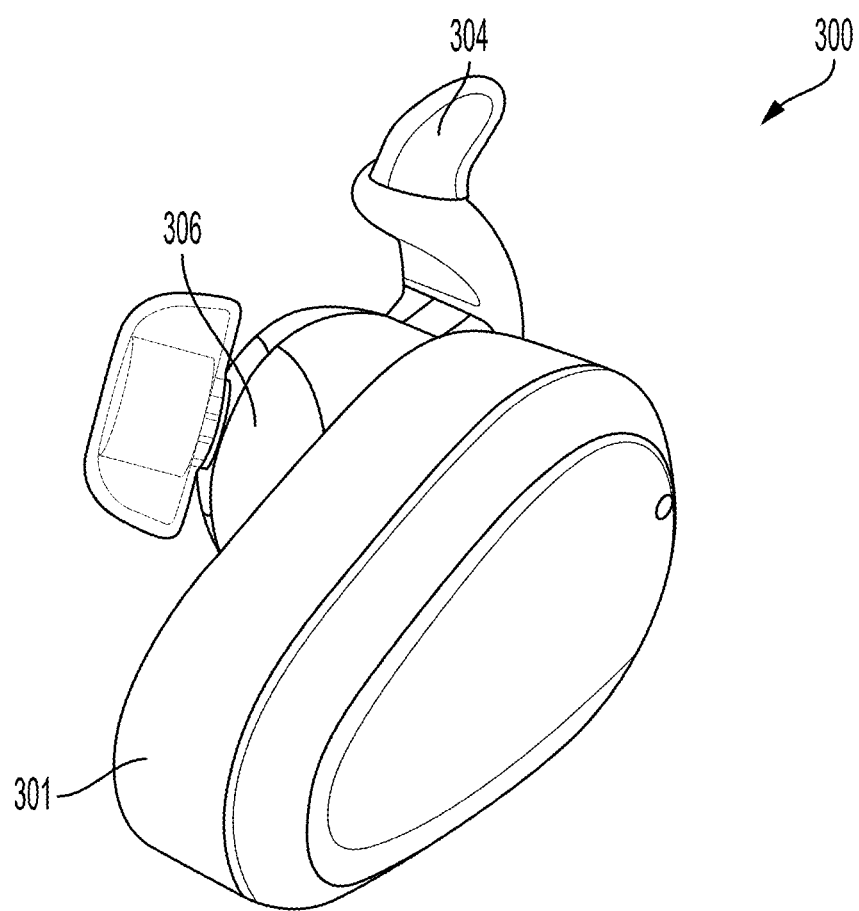
FIG. 3A depicts a perspective view of an earbud including a sensor assembly for detecting electrophysiologic signals, in accordance with an embodiment of the present disclosure.
Figure 3B:
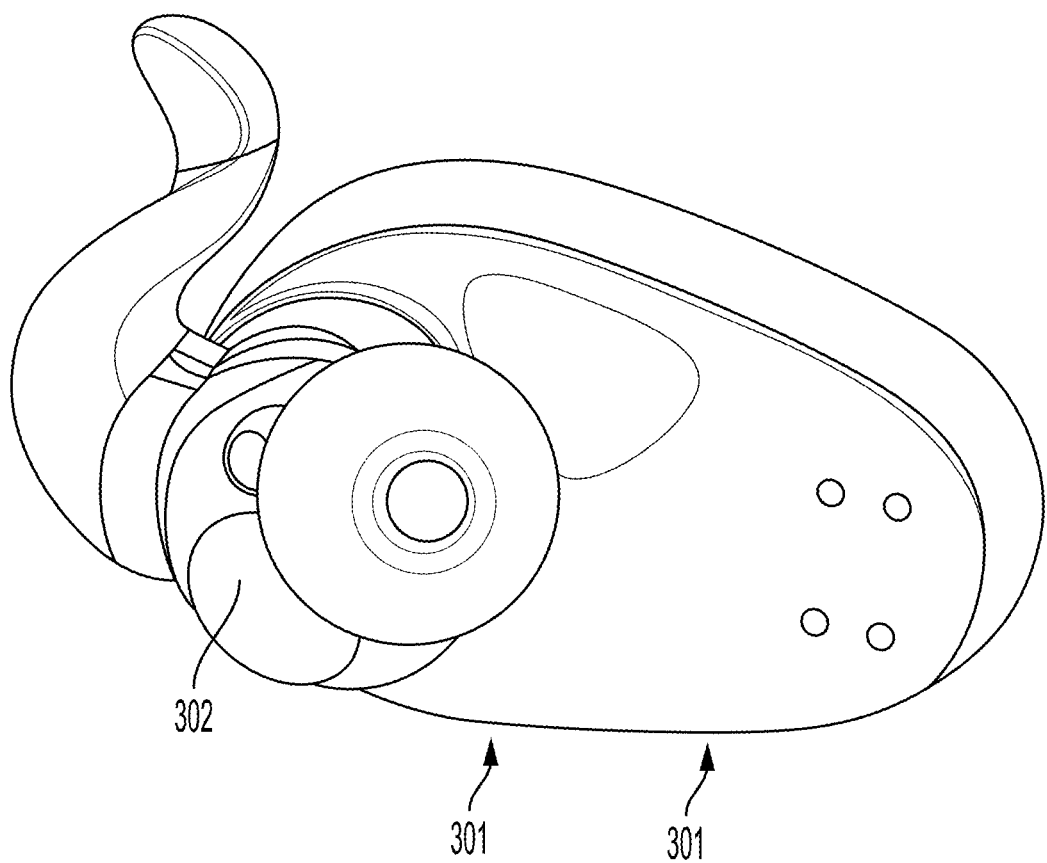
FIG. 3B depicts a reverse perspective view of the earbud shown in FIG. 3A, in accordance with an embodiment of the present disclosure.

In one embodiment shown in FIGS. 3A and 3B, an earbud 300 can include an electrode assembly including a series of electrodes that are positioned such that, when the earbud 300 is placed within a user's ear, each electrode physically contacts a particular anatomic location of the ear. In particular, the earbud 300 can include a first electrode 302 that is configured to contact a first anatomic location of the user's ear, a second electrode 304 that is configured to contact a second anatomic location of the user's ear, and a third electrode 306 that is configured to contact a third anatomic location of the user's ear. In various embodiments discussed in greater detail below, the various anatomic locations that the electrodes 302, 304, 306 are configured to contact could include the concha 402, the tragus 404, the triangular fossa 406, the helix 408, or various combinations thereof.

Figure 4A:
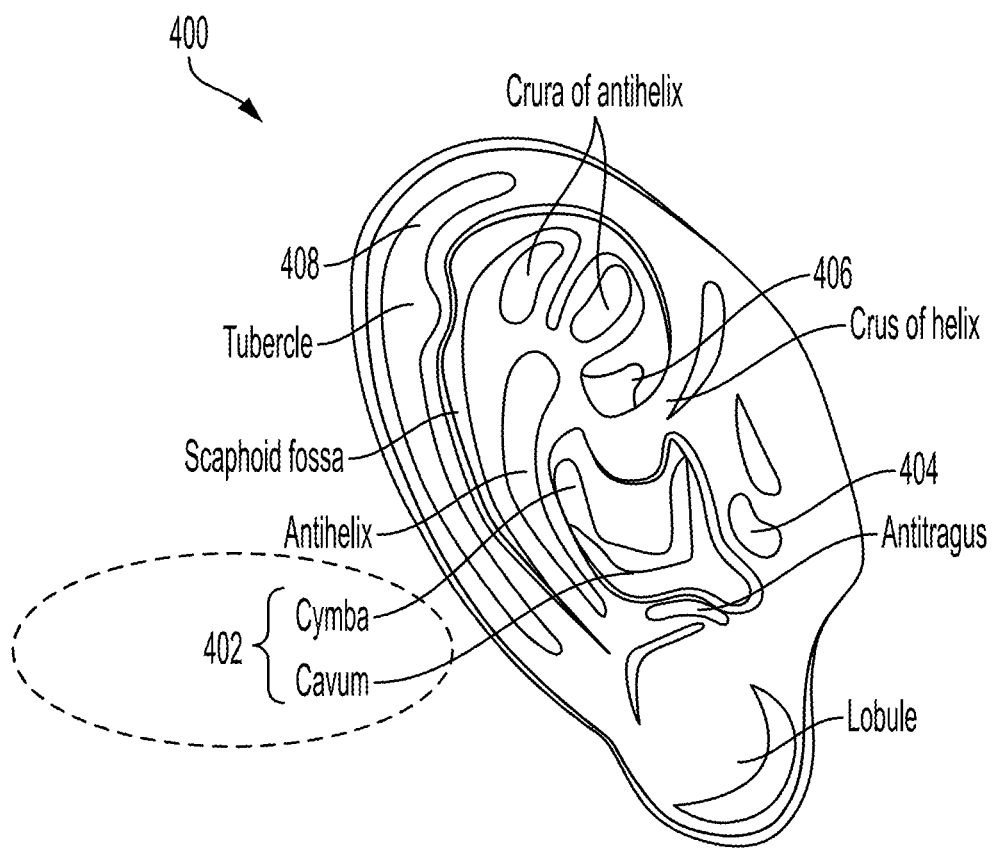
FIG. 4A depicts an anatomical diagram of an ear, in accordance with an embodiment of the present disclosure.
Figure 5:
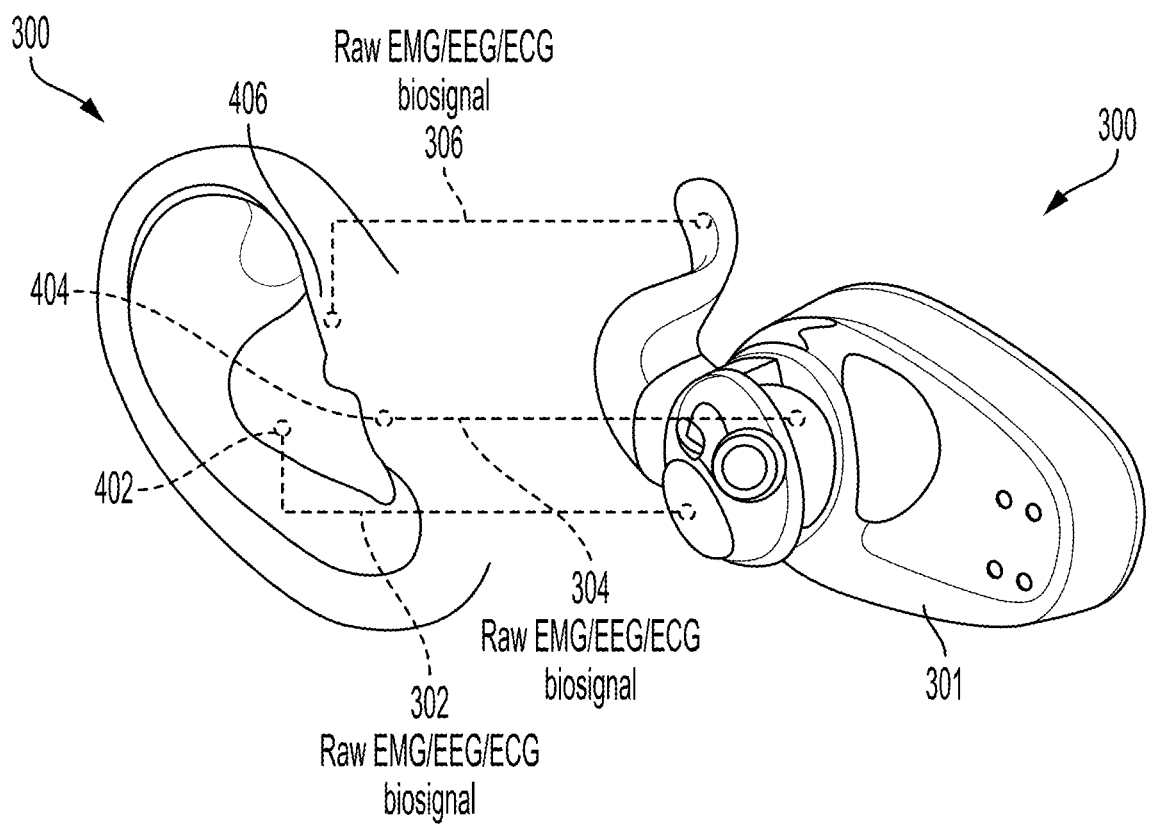
FIG. 5 depicts a diagram of the earbud sensor assembly indicating the anatomic locations of the ear corresponding to each electrode, in accordance with an embodiment of the present disclosure.

In one embodiment, the first electrode 302 can be positioned on the earbud housing 301 such it physically contacts the concha 402 (FIG. 4A) of the user's ear, the second electrode 304 can be positioned on the earbud housing 301 such it physically contacts the tragus 404 (FIG. 4A) of the user's ear, and the third electrode 306 can be positioned on the earbud housing 301 such it physically contacts the triangular fossa 406 (FIG. 4A) of the user's ear when the earbud 300 is worn therein, as shown in FIG. 5. In another embodiment, the first electrode 302 can be positioned on the earbud housing 301 such it physically contacts the concha 402 of the user's ear, the second electrode 304 can be positioned on the earbud housing 301 such it physically contacts the triangular fossa 406 of the user's ear, and the third electrode 306 can be positioned on the earbud housing 301 such it physically contacts the helix 408 (FIG. 4A) of the user's ear when the earbud 300 is worn therein. As will be discussed in greater detail below, the anatomic locations that the electrodes 302, 304, 306 are arranged to contact are selected based on a number of different factors, including the presence of different nerve types that are desirable for sensing particular types of electrophysiologic signals and maintaining a sufficient distance between the electrodes 302, 304, 306 such that noise across the electrodes 302, 304, 306 is minimized.

Figure 4B:
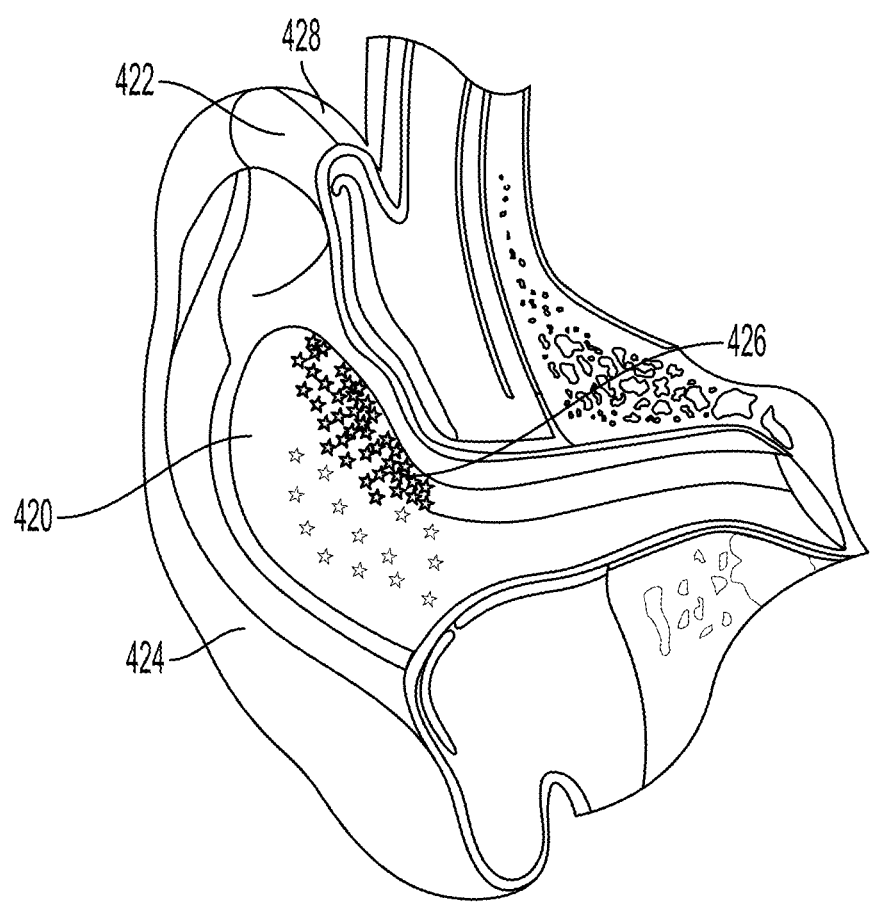
FIG. 4B depicts another anatomical diagram of an ear illustrating regions associated with various nerves, in accordance with an embodiment of the present disclosure.

FIG. 4B illustrates how different regions of the ear can be associated with different nerve types and, thus, suitable for sending electrophysiological signals associated with those different nerve types. In particular, the ear includes a first region 420 associated with the auricular branch of the vagus nerve, a second region 422 associated with the auriculotemporal nerve, a third region 424 associated with the greater auricular nerve, a fourth region 426 associated with the facial nerve (particular, the sensor branch thereof), and a fifth region 428 associated with the lesser occipital nerve. The electrodes 302, 304, 306 of the earbud 300 can be positioned in a manner such that they contact these regions associated with different nerve types depending on the types of electrophysiological signals that are being sensed. For example, it can be desirable to position one or more of the electrodes 302, 304, 306 such that they are able to sense signals associated with the auricular branch of vagus nerve (e.g., by contacting the first region 420 shown in FIG. 4B) and/or the auriculotemporal nerve (e.g., by contacting the second region 422 shown in FIG. 4B), among others.

As noted above, it is also desirable to maintaining a sufficient distance between the electrodes 302, 304, 306 such that noise across the electrodes 302, 304, 306 is minimized. The noise levels associated with various electrode configurations are assessed by analyzing the output waveform of each gesture that the earbud 300 is configured to identify across the various electrode positions. The signal-to-noise ratios (SNRs) for the gesture waveforms obtained via the various electrode configurations are calculated from empirical testing. The positioning and/or orientations of the electrodes 302, 304, 306 was can accordingly be adjusted for the earbud 300 in order to minimize the SNR for gesture detections.

In one embodiment, the first electrode 302 can serve as a primary sensor for detecting electrophysiologic signals exhibited by the user. In one embodiment, the second electrode 304 can detect a reference or baseline electrophysiologic signal exhibited by the user against which the signal detected by the first electrode 302 can be compared. In one embodiment, the third electrode 306 can be utilized to assist in the identification of common-mode signals across the set of electrodes 302, 304, 306. Once identified, common-mode signals across the set of electrodes 302, 304, 306 can be removed to isolate the targeted electrophysiologic signals or biosignals. In addition to contacting the desired anatomic locations, this positioning of the electrodes can be beneficial because it ensures that there is a sufficient amount of separation between each of the electrodes 302, 304, 306 such that signal noise is minimized.

The electrodes 302, 304, 306 can be positioned on the earbud housing 301 in a variety of different geometric positions or configurations to contact the corresponding anatomic locations, while accounting for anatomic variation between individuals. Studies have been performed that describe anatomical variations in individual's ears based on sex, age, ethnicity, and other factors. See, for example, Lee et al. (2018), "Anthropometric analysis of 3D ear scans of Koreans and Caucasians for ear product design," Ergonomics, 61(11), 1480-1495, which is hereby incorporated by reference herein in its entirety. Using such anatomical data, the electrodes 302, 304, 306 can be positioned and oriented on the earbud housing 301 in a variety of different ways such that they contact the corresponding anatomic locations of users' ears across a variety of different types of individuals. In some embodiments, the electrodes 302, 304, 306 can be constructed from a variety of different electrically conductive materials, including elastomers, silicone, metals, ceramics, carbon nanotube materials, composites thereof, or combinations thereof. In some embodiments, the electrodes 302, 304, 306 could include various coatings to enhance electrical conductivity, such as silver silver-chloride (Ag Ag—Cl), or improve skin contact characteristics. The size of the electrodes 302, 304, 306 can vary depending on design considerations accounting for anatomical variations between types of individuals, as well as the material of the electrodes 302, 304, 306. In some embodiments, the size of the electrodes 302, 304, 306 can be from, for example, 5-6 mm.

Referring now to FIGS. 4 and 5, there are shown an anatomical diagram of an ear 400 to illustrate the anatomical features referenced herein and a diagram indicating the anatomical features that each of the electrodes 302, 304, 306 are positioned to physically contact. As noted above, the first electrode 302 can be positioned to contact the concha 402 when the earbud 300 is positioned within the user's ear 400. It is beneficial for one of the electrodes in the electrode assembly to be positioned in this manner because the concha 402 exhibits a high density of nerves that correspond to neural/muscular activity. Further, the bowl shape of the concha 402 provides a large surface area for sensor contact, which in turn improves the ability to consistently and repeatably detect electrophysiologic signals at this location within the ear 400. Repeated lab tests have demonstrated that the concha 402 provides good signal-capturing quality with minimal noise deviation in the detected electrophysiologic signals. The second electrode 304 can be positioned to contact the tragus 404 when the earbud 300 is positioned within the user's ear 400. It is likewise beneficial for one of the electrodes in the electrode assembly to be positioned in this manner because it is desirable to the reference electrode to be placed at a location within the ear 400 that exhibits low or zero electrophysiologic signal activity. Therefore, the second electrode 304 can sense a reference or baseline electrical signal that can be used to properly identify the electrophysiologic activity sensed by the first electrode 302. Lab tests have demonstrated that the tragus 404 exhibits such low or zero electrophysiologic signal activity that is desirable for the reference electrode. Therefore, it can be beneficial for the second electrode 304 to be positioned on the housing 301 of the earbud 300 such that it contacts the tragus 404. The third electrode 306 can be positioned to contact the triangular fossa 406 when the earbud 300 is positioned within the user's ear 400. It is likewise beneficial for one of the electrodes of the electrode assembly to be positioned in this manner because it can be desirable for the bias electrode to be positioned in an area of low or zero electrophysiologic signal activity that is likewise physically separated from the first electrode 302 and the second electrode 304. Lab tests have demonstrated that the triangular fossa 406 exhibits such low or zero electrophysiologic signal activity that is desirable for the bias electrode and, further, is physically separated from the other two locations at which electrodes are positioned (i.e., the concha 402 and the tragus 404). Therefore, it can be beneficial for the third electrode 306 to be positioned on the housing 301 of the earbud 300 such that it contacts the triangular fossa 406.

Additionally, the aforementioned positioning of the electrodes 302, 304, 306 is beneficial because it allows each of the electrodes 302, 304, 306 to contact a different area of the ear 400 that correspond to different concentrations of nerves. The auricular branch of the vagus nerve extends to the concha 402, which the first electrode 302 is configured to contact. Accordingly, the first electrode 302 can be configured to sense electrophysiologic signals associated with this branch of the vagus nerve. Further, the greater auricular nerve extends to the tragus 404, which the second electrode 304 is configured to contact. Accordingly, the second electrode 304 can be configured to sense electrophysiologic signals associated this branch of the vagus nerve. Finally, the auriculotemporal nerve extends to the fossa 406, which the third electrode 306 is configured to contact. Accordingly, the third electrode 306 can be configured to sense electrophysiologic signals associated with the auriculotemporal nerve. Further, because the first electrode 302 and the second electrode 304 sense different branches of the same nerve (e.g., the vague nerve), it can be beneficial for the third electrode 306 to contact a different nerve (e.g., the auriculotemporal nerve) in order to facilitate the identification and removal of noise from the electrophysiologic signals sensed by first electrode 302 and the second electrode 304.

In sum, the sensor assemblies described herein are beneficial because they maintain physical contact with specific locations in or on the user's ear 400 that are ideally suited to allow the electrode assembly to detect particular types of electrophysiologic signals and avoid obstructions (e.g., as hair or ear wax) that would impede signal quality. Further, the electrodes 302, 304, 306 are positioned on the earbud 300 to maintain physical contact with the corresponding anatomic locations of the ear 400 with adequate force such that signal quality is not impaired. The electrodes 302, 304, 306 are maintained in physical contact with the corresponding anatomic locations of the ear 400 through a mechanical design that interacts with human ear morphology structures in a way that keeps it in place for most of the population. The size, shape, and material properties (e.g., flexibility and surface friction) of the electrodes 302, 304, 306 allows them to maintain contact with the skin as the earbud 300 is worn by the user. Further, the electrodes 302, 304, 306 are positioned such that they can accommodate anatomical variations in individuals' ears 300 due to variation in individuals' size, sex, and so on.

The electrodes 302, 304, 306 can be positioned or biased to contact the desired anatomic locations of the user's ear 400 in a variety of different manners. In one embodiment, the electrodes 302, 304, 306 can be coextensive with or positioned on the surface of the housing 301 of the earbud 300. In another embodiment, the electrodes 302, 304, 306 can be positioned at the end of spring arms that extend from the earbud 300 and are biased to contact the user's ear 400. In some embodiments, the electrodes 302, 304, 306 can include conductive rubber tips that are designed to frictionally engage the user's ear 400 in a comfortable manner. In another embodiment, the electrodes 302, 304, 306 can include conductive rubber suction cups that are configured to secure the electrodes 302, 304, 306 in place against the user's ear 400. In another embodiment, the electrodes 302, 304, 306 can include reusable and/or replaceable sensor pads having an adhesive is configured to secure the electrodes 302, 304, 306 in place against the user's ear 400. In another embodiment, the earbud 300 can include a deformable pad that is configured to deform to fit the interior shape of the ear 400 to maintain contact the electrodes 302, 304, 306 in contact with their corresponding anatomic locations. In yet another embodiment, the earbud 300 can include mechanical clips associated with one or more of the electrodes 302, 304, 306 that are configured to maintain the respective electrode(s) at the corresponding anatomic locations.

Figure 6:
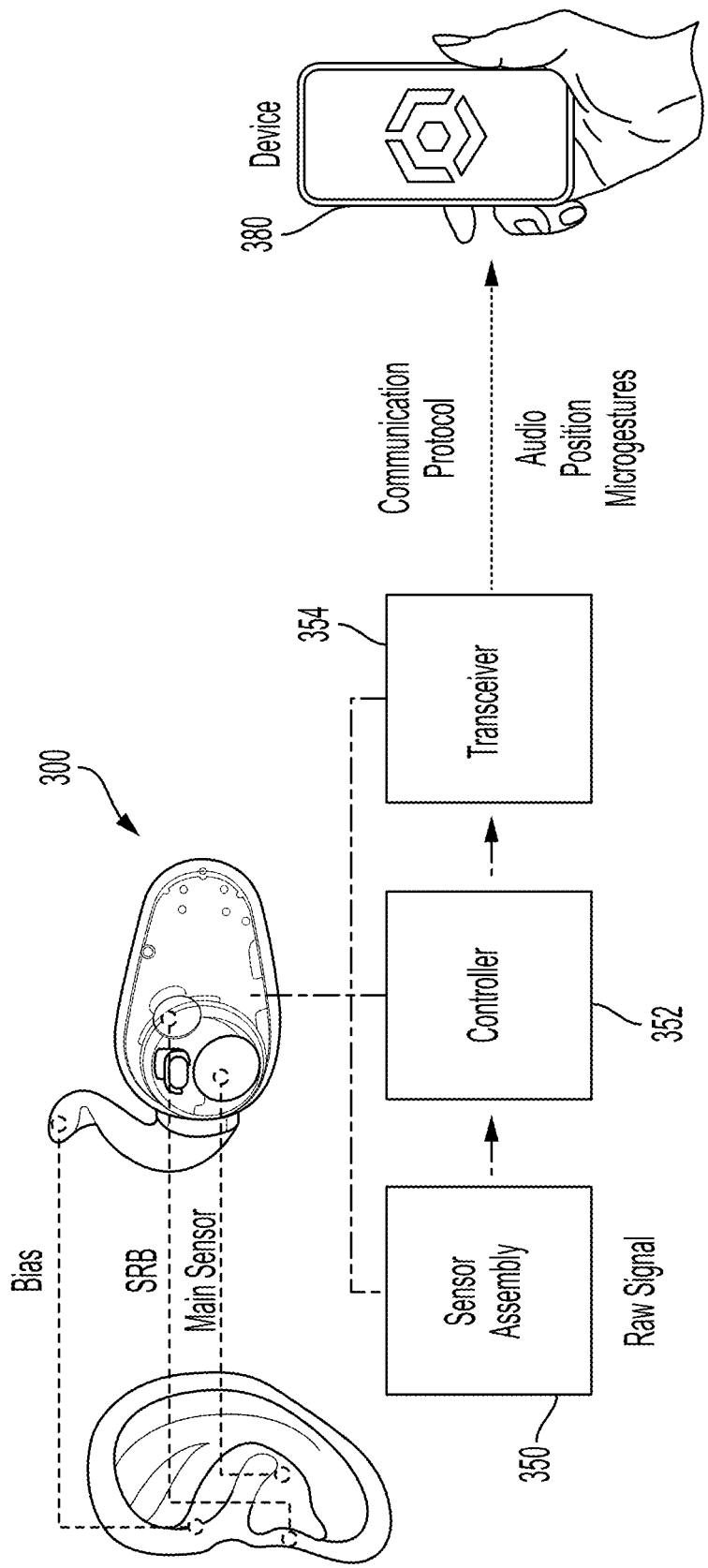
FIG. 6 depicts a diagram of a system incorporating the earbud shown in FIGS. 3A, 3B, and 5, in accordance with an embodiment of the present disclosure.

Referring now to FIG. 6, there is shown a block diagram of the earbud 300. In this embodiment, the earbud 300 includes the electrode assembly 350 (e.g., the first electrode 302, the second electrode 304, and the third electrode 306) that detects the raw electrophysiologic signal from the user. The electrode assembly 350 is communicably coupled to a controller 352 that is adapted identify gestures being performed by the user from the raw electrophysiologic signal data. The controller 352 can include software, hardware, firmware, or any combination thereof that is programmed or adapted to perform the described functions. In one embodiment, the controller 352 can include a processor coupled to a memory, wherein the processor is configured to execute instructions stored in the memory to perform the described functions and/or steps. In another embodiment, the controller 352 can include an application-specific integrated circuit (ASIC) or field-programmable array (FPGA) that is designed to perform the described functions and/or steps in response to inputs thereto. The earbud 300 can further include a transceiver 354 that can communicate the detected gestures (e.g., as identified via the controller 352) via a wireless communications protocol (e.g., Bluetooth) to an external device 380 (e.g., a smartphone or laptop). In some embodiments, the external device 380 can include a virtual reality headset, which is described in further detail below. The external device 380 can then take a variety of different actions in response to the received gesture, such as displaying particular content (or changing which type of content is displayed), changing a mode or function being executed by the external device 380, and so on.

The controller 352 can identify gestures based on the time varying magnitude of the electrophysiologic signals sensed via the electrodes 302, 304, 306 and/or gestural signals. The time variance of the electrophysiologic signals result from the synchronous activity neurons at the locations at which the electrodes 302, 304, 306 are positioned, which in turn corresponds to muscular movements resulting from the actions of the neurons. Accordingly, the electrophysiologic signals sensed by the electrodes 302, 304, 306 can be used to identify muscular movements by the user, which in turn can be used to identify the gestures being performed by the user. A variety of different gestures can be identified using the various embodiments of the system described herein, including jaw clenches, opening and closing of the mouth, forced eye blinks (i.e., eye blinks caused via the somatic nervous system as opposed to the autonomic nervous system), eyebrow raises, and leg tapping. In some embodiments, the controller 352 can implement a machine learning algorithm trained to identify different gestures being performed by the user from the electrophysiologic and/or gestural data. In one embodiment, the machine learning algorithm could include a random forest (e.g., an XGBoost random forest).

Figure 7:
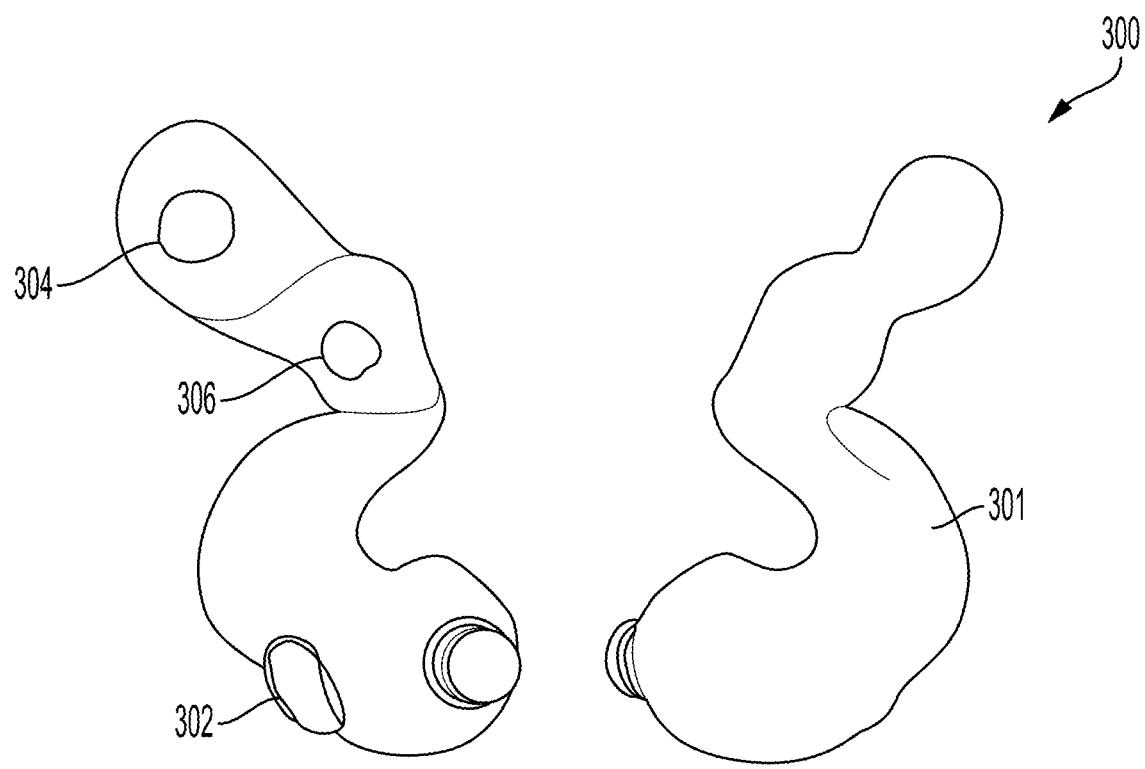
FIG. 7 depicts an alternative embodiment of an earbud including a sensor assembly for detecting electrophysiologic signals, in accordance with an embodiment of the present disclosure.

It should further be noted that the various embodiments and configurations of the earbud 300 shown in FIGS. 3A-6 are simply provided for illustrative purposes. The earbud 300, earbud housing 301, and electrodes 302, 304, 306 can be arranged in a number of different configurations, sizes, or shapes, such as with the alternative embodiment of the earbud 300 illustrated in FIG. 7.

Example—Virtual Reality Headset Control

Figure 8:
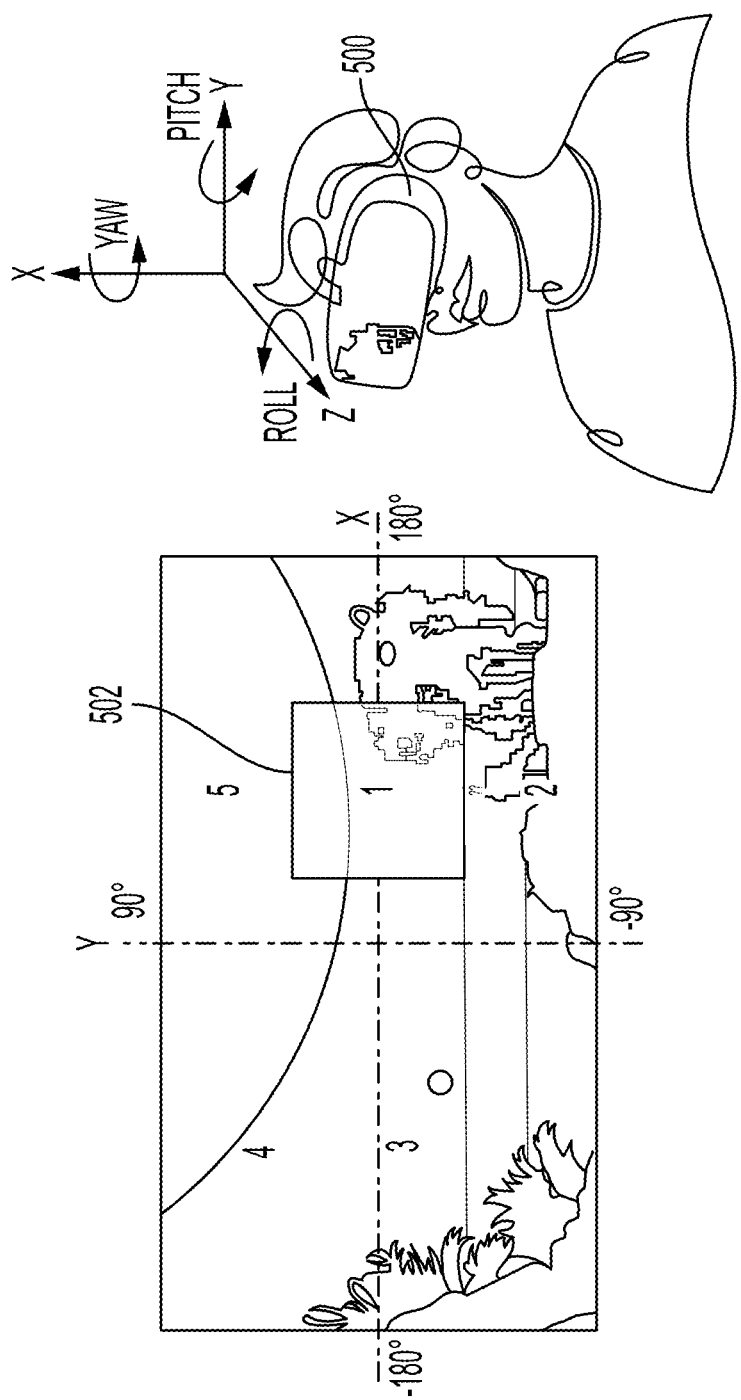
FIG. 8 depicts a diagram indicating how a virtual reality headset could be controlled in response to gesture identified via the earbud sensor assembly, in accordance with an embodiment of the present disclosure.

As noted above, the earbud 300 can transmit identified gestures to an external device 380 for use in controlling the external device 380 or a feature of the external device 380. In one illustrative application shown in FIG. 8, the external device 380 can include a virtual reality headset 500 or an augmented reality headset. In this embodiment, the gestures detected via the earbud 300 could be used to control a variety of different aspects of the virtual reality headset 500, such as the field of view (FOV) 502 displayed thereby or the mode that the virtual reality headset 500 is in (e.g., an observation mode or a movement mode). For example, if the virtual reality headset 500 is in an observation mode, if the user was initially looking at point (1), the FOV 502 that has point (1) as its center would be transmitted to the display of the virtual reality headset 500. If the user then moved his or her head to look at point (2), the FOV 502 would move on the display of the virtual reality headset 500 until point (2) would be the center of the user's vision in response to the detected change in the user's head position (e.g., via the electrode assembly 350). The direction in which the user is looking could be determined via, for example, a gestural sensor 103, such as an accelerometer or a gyroscope. In one embodiment, the change in head position could be sensed along three axes, namely, roll, pitch, and yaw. The system could accordingly calculate the orientation of the user's head using a variety of different techniques, including Euler angles or quaternions.

As another example, the gestures detected via the earbud 300 could be utilized to change between different modes, such as a movement mode in which the user's avatar moves through the virtual environment in response to detected gestures by the user or an observation mode in which the user's avatar maintains position within the virtual environment and instead the user's FOV 502 is changed as in response to detected gestures by the user. A variety of different gestures could be detected to change between different modes. For example, in the movement mode, if the user pitched his or her head down towards point (2), the FOV 502 would still be fixed on point (1), but the FOV 502 would update to show forward movement within that virtual space. Further, the speed of forward movement would increase as the head's downward offset from point (1) increases. Conversely, if the virtual reality headset 500 was in the observation mode, if the user pitched his or her head down towards point (2), the FOV 502 would be updated such that it was centered on point (2).

This disclosure is not limited to the particular systems, devices and methods described, as these may vary. The terminology used in the description is for the purpose of describing the particular versions or embodiments only and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" include plural references, unless the context clearly dictates otherwise. Thus, for example, reference to a "protein" is a reference to one or more proteins and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of".

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An earbud comprising:
a gestural sensor configured to detect movement data indicative of a gesture being performed by a user;
a first electrode positioned to physically contact a concha of an ear of the user when the earbud is worn by the user;
a second electrode positioned to physically contact a tragus of the ear when the earbud is worn by the user;
a third electrode positioned to physically contact a triangular fossa of the ear when the earbud is worn by the user; and
a controller coupled to the gestural sensor, the first electrode, the second electrode, and the third electrode, the controller programmed to:
receive an electrophysiologic measurement from each of the first electrode, the second electrode, and the third electrode, wherein a first electrophysiological measurement from the first electrode corresponds to an electrophysiological signal indicative of the gesture being performed by the user, a second electrophysiological measurement from the second electrode corresponds to a baseline electrophysiological signal, and a third electrophysiological measurement from the third electrode corresponds to a common mode signal,
determine the gesture being performed by the user based on (i) a comparison of the electrophysiological signal indicative of the gesture to the baseline electrophysiological signal and the common mode signal and (ii) the movement data from the gestural sensor, and
transmit the determined gesture to an external device for control thereof.

2. The earbud of claim 1, wherein the electrophysiologic measurements are selected from the group consisting of, electrocardiogram (ECG), an electroencephalogram (EEG), or an electromyography (EMG).

3. The earbud of claim 1, wherein each of the first electrode, the second electrode, and the third electrode comprise a size from about 5 mm to about 6 mm.

4. The earbud of claim 1, wherein the external device comprises a virtual reality headset.

5. The earbud of claim 1, wherein each of the first electrode, the second electrode, and the third electrode comprise at least one of an elastomer, silicone, a metal, a ceramic, a carbon nanotube material, composites thereof, or combinations thereof.

6. A system comprising:
an earbud comprising:
a gestural sensor configured to detect movement data indicative of a gesture being performed by a user,
a first electrode positioned to physically contact a concha of an ear of a user when the earbud is worn by the user,
a second electrode positioned to physically contact a tragus of the ear when the earbud is worn by the user,
a third electrode positioned to physically contact a triangular fossa of the ear when the earbud is worn by the user, and
a controller coupled to the gestural sensor, the first electrode, the second electrode, and the third electrode, the controller programmed to:
receive an electrophysiologic measurement from each of the first electrode, the second electrode, and the third electrode, wherein a first electrophysiological measurement from the first electrode corresponds to an electrophysiological signal indicative of the gesture being performed by the user, a second electrophysiological measurement from the second electrode corresponds to a baseline electrophysiological signal, and a third electrophysiological measurement from the third electrode corresponds to a common mode signal, and
determine the gesture being performed by the user based on (i) a comparison of the electrophysiological signal indicative of the gesture to the baseline electrophysiological signal and the common mode signal and (ii) the movement data from the gestural sensor; and
an external device communicably coupled to the earbud, the external device programmed to:
receive the determined gesture from the controller of the earbud, and
perform an action in response to the determined gesture.

7. The system of claim 6, wherein the electrophysiologic measurements are selected from the group consisting of, electrocardiogram (ECG), an electroencephalogram (EEG), or an electromyography (EMG).

8. The system of claim 6, wherein each of the first electrode, the second electrode, and the third electrode comprise a size from about 5 mm to about 6 mm.

9. The system of claim 6, wherein the external device comprises a virtual reality headset.

10. The system of claim 9, wherein the action comprises at least one of changing a field of view of the virtual reality headset or changing a mode of the virtual reality headset.

11. The system of claim 6, wherein each of the first electrode, the second electrode, and the third electrode comprise at least one of an elastomer, silicone, a metal, a ceramic, a carbon nanotube material, composites thereof, or combinations thereof.

12. The earbud of claim 1, wherein the gestural sensor comprises at least one of a gyroscope, an accelerometer, or a pressure sensor configured to detect an inner ear pressure of the user.

13. The system of claim 6, wherein the gestural sensor comprises at least one of a gyroscope, an accelerometer, or a pressure sensor configured to detect an inner ear pressure of the user.

* * * * *